United States Patent
Brinz et al.

(10) Patent No.: US 8,235,953 B2
(45) Date of Patent: Aug. 7, 2012

(54) METERING DEVICE AND METHOD FOR OPERATING SAME

(75) Inventors: Thomas Brinz, Teck (DE); Jane Lewis, Wales (GB); Markus Tiefenbacher, Fellbach-Schmiden (DE); Thomas Geiger, Walddorfhaeslach (DE)

(73) Assignee: Robert Bosch GmbH, Stuttgart (DE)

( * ) Notice: Subject to any disclaimer, the term of this patent is extended or adjusted under 35 U.S.C. 154(b) by 1601 days.

(21) Appl. No.: 11/435,431

(22) Filed: May 16, 2006

(65) Prior Publication Data
US 2006/0264817 A1 Nov. 23, 2006

(30) Foreign Application Priority Data
May 19, 2005 (DE) .................... 10 2005 023 188

(51) Int. Cl.
*A61M 5/315* (2006.01)
*A61M 37/00* (2006.01)
(52) U.S. Cl. .......................... 604/231; 604/82
(58) Field of Classification Search .............. 604/82, 604/231, 232
See application file for complete search history.

(56) References Cited

U.S. PATENT DOCUMENTS

| | | | |
|---|---|---|---|
| 2,475,060 A | 7/1949 | Smith | |
| 3,563,415 A * | 2/1971 | Ogle | 222/145.4 |
| 3,722,512 A * | 3/1973 | Hein et al. | 604/231 |
| 4,657,534 A * | 4/1987 | Beck et al. | 604/90 |
| 4,741,737 A | 5/1988 | Meyer et al. | |
| 4,772,271 A | 9/1988 | Meyer et al. | |
| 5,015,229 A | 5/1991 | Meyer et al. | |
| 5,277,198 A | 1/1994 | Kanner et al. | |
| 6,811,688 B1 | 11/2004 | Hofmann | |
| 6,936,033 B2 * | 8/2005 | McIntosh et al. | 604/191 |
| 2005/0261625 A1 | 11/2005 | Ashman | |

FOREIGN PATENT DOCUMENTS
WO    WO 00/43057    7/2000

* cited by examiner

*Primary Examiner* — Nicholas Lucchesi
*Assistant Examiner* — Rebecca E Eisenberg
(74) *Attorney, Agent, or Firm* — Kenyon & Kenyon LLP

(57) ABSTRACT

A metering device, a metering element, and a method for operating same, the metering element having a storage container open on one side for receiving the substances to be metered and a plunger which is axially movable and reversibly seals the opening of the storage container and which preferably has at least one centrally located metering opening for metering the substances provided in the storage container, the plunger including a separation device for particles.

10 Claims, 3 Drawing Sheets

METERING DEVICE AND METHOD FOR OPERATING SAME

FIELD OF THE INVENTION

The present invention relates to a metering element, a metering device, and a method for operating same.

BACKGROUND INFORMATION

Discovery and development of new substances and materials represent paramount goals in materials science, chemistry, and pharmaceutics. However, the search for suitable compounds frequently involves great expenses in terms of both financial means and time. In order to carry out this search in a more efficient and more cost-effective way, a systematic methodology, which became known as "Combinatorial Chemistry," had been introduced years ago in pharmaceutics and subsequently also in other areas of application. Multiple potentially interesting compounds are produced and analyzed in this method. The possibility of automation, which allows for great throughput capacities in the shortest time, is to be considered the advantage of this method.

For generating the necessary materials libraries, a great number of potentially interesting substances or their precursor compounds must be positioned or metered at defined points of appropriate substrates. Due to the typically great number of substances to be metered, this is carried out fully automatically.

In particular in manufacturing of formulations such as paints, adhesives, pesticides, screen-printing pastes, etc., grinding balls or glass beads are added to the formulation and agitated via rapid and vigorous shaking and turning for better mixing results and for disintegrating particles. Due to the rapid acceleration of the balls, the particles are disintegrated at the impact of the balls. This process is referred to as dispersion.

After dispersing or mixing, the dispersion (formulation), containing the grinding balls or glass beads, is mostly fed to a screen for separating the balls. The remaining formulation is rinsed from between the grinding balls or glass beads by using an additional solvent. Appropriate grinding balls are typically made of glass, ceramic, or metal.

For use in combinatorial chemistry, this method is very difficult to automate, since a new or cleaned screen must be installed for each formulation, for example. Furthermore, a final rinsing process requires an additional metering unit. Moreover, handling a formulation containing heavy balls for feeding it to a screen is not easy to implement.

An object of the present invention is to provide a metering element, a metering device, and a method for operating same which allow an automated dispersing, mixing, or grinding procedure which is suitable for use in combinatorial chemistry.

SUMMARY OF THE INVENTION

The metering device and metering element, as well as the method for operating same have the advantage that the object on which the present invention is based is achieved in an advantageous manner. This is particularly based upon the fact that the metering element has a storage reservoir in which a proper dispersing, mixing, or grinding procedure may be carried out and which allows simple separation of the treated dispersion from corresponding disintegrating or mixing means.

The metering element advantageously has a plunger, which is axially movable and reversibly seals the opening of the storage reservoir, and which includes a separating device for coarse particles, grinding means, and mixing means in the form of a screen, a magnet, or an annular gap positioned in front of the metering opening. In this way, disintegrating or mixing means may be separated from the resulting dispersion without a cleaning step of a screen, for example, or transfer into a collecting container being necessary prior to actual metering.

Furthermore, the plunger is advantageously connected to a piston skirt which has a metering line for metering the provided substances and which may be provided with an exchangeable metering needle on its end facing away from the plunger. The metering needle is connected to the piston skirt via a luer lock, for example. The exchangeability of the metering needle is advantageous, since the metering element may be adapted in a simple manner with respect to the required metering quantities and to the volume flow required for metering, and since the viscosity of the substances to be metered may be taken into account in this way. Since one storage container having its own plunger is preferably assigned to each of the substances to be metered, any possibility of contamination with foreign substances is thereby eliminated.

In another advantageous embodiment, the metering device includes multiple metering elements whose storage containers have an essentially identical longitudinal extension and different diameters. In this way, different volumes may be implemented in the storage containers without requiring an adaptation of the automatic gripper device. It is advantageous in this case when the respective receptacle of the storage container or of the plunger has a coding for identifying the volume or the diameter of the associated storage container.

Furthermore, it is advantageous when a plurality of metering elements is combined into one metering device and when a means for synchronous shaking and/or swaying of the metering elements is provided since a plurality of different dispersions may be synchronously produced in this way.

DETAILED DESCRIPTION

The idea on which the present invention is based is to provide a metering element or a metering device which makes efficient and automated metering of a plurality of substances necessary for establishing combinatorial material libraries possible, in particular within the scope of combinatorial material development.

Figure 1:
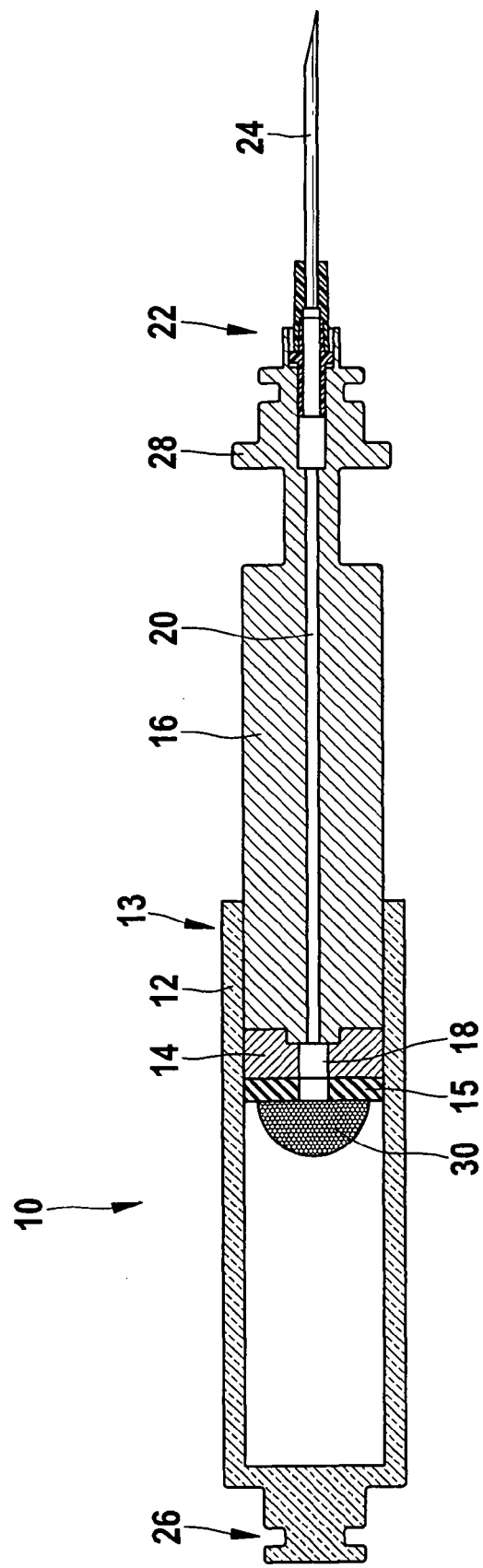
FIG. 1 shows a sectional representation of a metering element.

The core of the metering device is/are one or multiple metering elements as illustrated in FIG. 1. Metering element 10 includes a storage container 12 in which one or multiple substances to be metered may be provided. Storage container 12 is made of an essentially chemically inert material, such as glass, PTFE, or PVC. Storage container 12 has preferably a cylindrical design, one end of storage container 12 being open and able to be sealed by an axially movable plunger 14. In order to ensure the sealability of storage container 12 independently from plunger 14, storage container 12 has a thread 13 impressed on the exterior wall of storage container 12 or is provided with a mechanical push-in one-time lock.

Plunger 14 preferably has a seal 15 on the side facing the substance to be metered, the seal being mechanically fixed and is thus of an exchangeable design. On the side facing away from the substance to be metered, plunger 14 merges into a piston skirt 16 which has preferably four suitable ribs for better guidance. Plunger 14 as well as piston skirt 16 is preferably made of high-grade steel or a chemically inert polymer such as PTFE or PVC.

A distinctive feature of metering element 10 is that, in contrast to the conventional metering syringes primarily known from the medical field, metering of the supplied substances (preferably) takes place through an opening 18 of plunger 14. For this purpose, piston skirt 16, connected to plunger 14, has a metering line 20 through which a substance to be metered may be transported from storage container 12 through opening 18. On the side facing away from plunger 14, piston skirt 16 has a mechanical fixing device 22 for a metering needle 24, for example. Mechanical fixing device 22 is preferably designed as a luer lock.

A pouring device, a hollow line, or a plunger having a widened diameter may also alternatively be attached instead of a metering needle 24 or the metering element may be fixedly connected to a closed metering apparatus or reaction apparatus.

In order to ensure automated metering in a short time cycle, storage container 12 has, on its side opposite the opening, and/or plunger 14 or piston skirt 16 has/have on the side facing away from the substance to be metered a receptacle or fitting 26, 28 which is used as the contact point for a mechanical gripper device.

Different metering elements may be used which differ with respect to the possible metering volume in particular. Despite differing volumes of storage containers 12, the length of metering element 10 is largely kept constant. Different volumes are achieved through the selection of appropriate diameters of storage container 12. This makes it possible that metering elements 10 having differing metering volumes may be successively used for metering without requiring an adaptation of the mechanical gripper device. In addition, there is the possibility to design receptacles 26, 28 or the outer surface of storage container 12 in the form of a printed bar code in such a way that they have an identifier for identifying the metering volume so that the mechanical gripper device is automatically adapted to the corresponding metering volume of the metering element just installed.

For metering, a separate metering element is preferably assigned to each substance or substance mixture to be metered. This effectively prevents intermixing or contamination of the substances. For filling metering element 10, its plunger 14 is initially removed and the substance is supplied to open storage container 12. Plunger 14 is then inserted into storage container 12 and the air present there may escape via metering line 20. If, however, the supplied substance is an air-sensitive compound, the substance may be supplied in an inert gas apparatus or a substance already supplied may be degassed in a normal manner via metering line 20.

If particle-containing dispersions, in particular coarse particle-containing dispersions, are supplied to storage container 12 of metering element 10, a separation means, e.g., in the form of a screen 30, is added to metering element 10 for separating the particles. This screen is preferably mechanically connected to plunger 14 and is situated upstream from opening 18 or metering line 20 in the flow direction of the dispersion.

Figure 2:
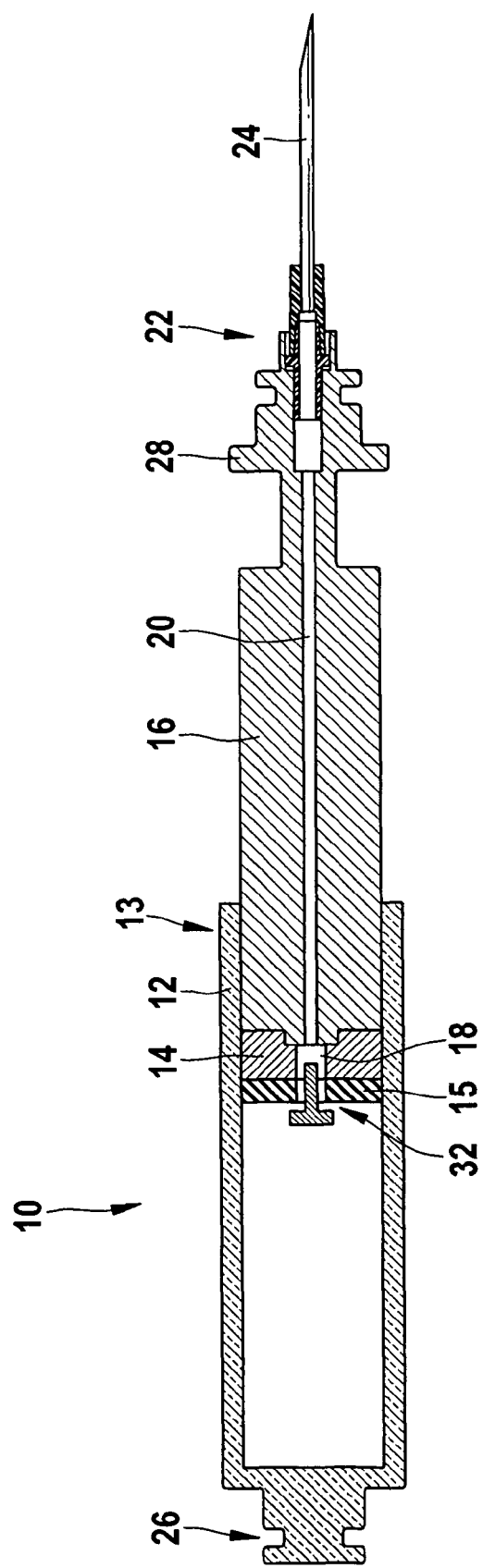
FIG. 2 shows a variant of the metering element shown in FIG. 1.

One alternative embodiment is illustrated in FIG. 2, the same reference numerals indicating the same components as in FIG. 1.

Metering element 10 illustrated in FIG. 2 includes, instead of a screen 30, an annular gap 32 whose flow-through gap diameter is adapted to the diameter of the particles to be separated and may possibly also have a variable design. Instead of a screen 30 or an annular gap 32 or in addition thereto, the metering element may have a magnet for separating magnetic particles.

For metering dispersions, preferably a substance to be dispersed, a disperging agent as well as a grinding means or a mixing means are initially supplied to storage container 12 of metering device 10. Balls made of metal, glass, or ceramic are suitable as grinding means or mixing means, for example. Depending on the used crushing, disperging, or mixing methods and depending on the requirement of the supplied substances with respect to vapor pressure, air sensibility, etc., storage container 12 is subsequently sealed using a temporary lock or plunger 14.

Figure 3A:
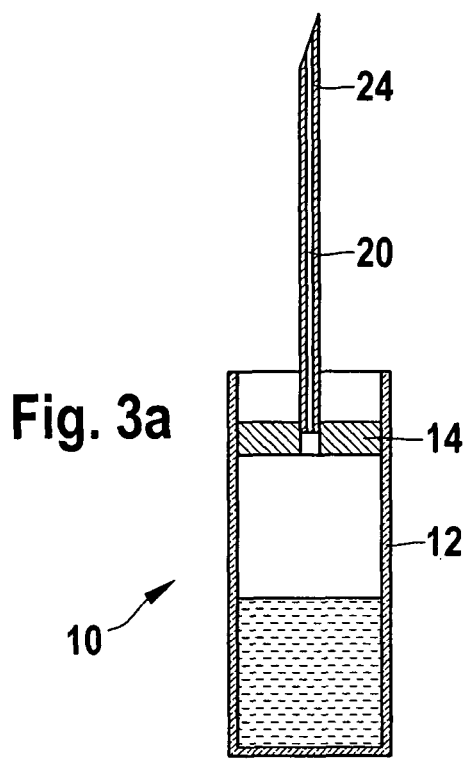
FIGS. 3a through 3d show schematic steps of a method for metering substances.

Individually or in tandem with other metering elements of the metering device, metering element 10 is preferably subjected to a strong rotating or shaking motion. After dispersion, grinding, or mixing is completed, the created dispersion is separated from the added grinding means or mixing means and/or from other types of undesirable coarse particles. For this purpose, the possibly present temporary lock is removed and plunger 14 is inserted into storage container 12 (see FIG. 3a).

Figure 3B:
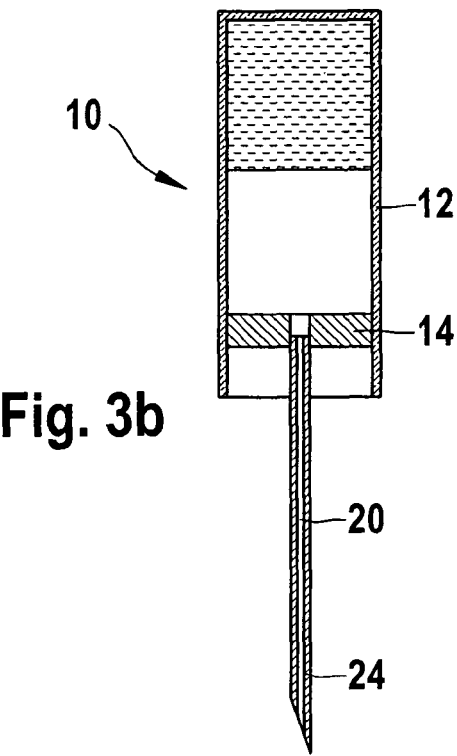
Figure 3C:
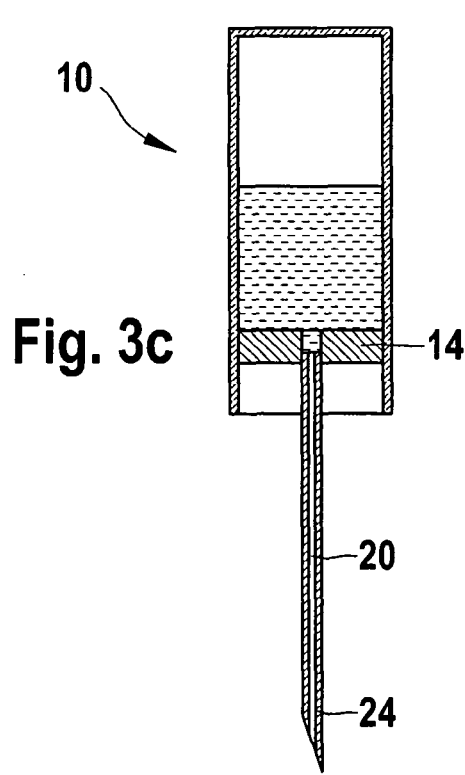
Figure 3D:
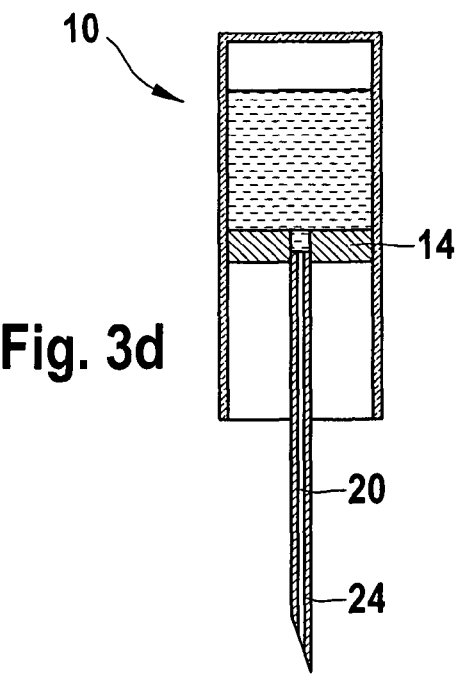

Plunger 14 is preferably inserted into storage container 12 only to the point where a sufficient air cushion remains inside of storage container 12. Subsequently, the metering element is preferably turned 180° (see FIG. 3b). In the process, the formulation or dispersion together with the grinding means or mixing means flows downward and the air cushion is displaced upward (see FIG. 3c). If plunger 14 is now pushed into storage container 12, the air presses the formulation through separation means 30, 32 and out of storage container 12 via opening 18 or metering line 20 (see FIG. 3d). The grinding means or the mixing means is retained by separation means 30, 32.

The formulation or dispersion may subsequently be directly calibrated to the substrate of a combinatorial material library and tested or it may be filled as a master batch into another metering element for further use.

In a further embodiment, metering element 10 is additionally used as a chemical reactor. The substances supplied to storage container 12 of metering element 10 are subjected to a chemical reaction. For this purpose, metering element 10 may have an appropriate heating, agitating, or cooling device. These devices may also be designed, however, as being temporarily attachable or as just being available.

In order to be able to provide a plurality of dispersions in a time-saving manner, a plurality of metering elements, e.g., 16 to 256, are inserted into a metering device, held there, preferably filled in parallel, and synchronously shaken or rotated. For metering, the metering elements may be removed automatically either individually or in groups and their content is conveyed to its destination.

What is claimed is:

1. A metering element comprising:
   a storage container open on one side for receiving the substances to be metered; and
   a plunger which is axially movable and reversibly seals an opening of the storage container, and which has at least one centrally located metering opening for metering the substances in the storage container, the plunger including a separation device for particles wherein the storage container has a receptacle opposite the opening.

2. The metering element according to claim 1, wherein the substances are metered for creating combinatorial materials libraries.

3. The metering element according to claim 1, wherein the separation device is designed as one of a screen, a magnet, and an annular gap.

4. The metering element according to claim 1, wherein the separation device is situated upstream from the metering opening.

5. The metering element according to claim 1, wherein at least one of the storage container and the plunger includes a receptacle used as a contact point for a mechanical gripper device.

6. The metering element according to claim 5, wherein the plunger is connected to a piston skirt which has a metering line for metering the substances, and the receptacle is attached to its end facing away from the plunger.

7. The metering element according to claim 6, wherein the piston skirt is connected at its end facing away from the plunger to an exchangeable metering needle.

8. A metering device comprising a plurality of metering elements, each of the metering elements including:
- a storage container open on one side for receiving the substances to be metered; and
- a plunger which is axially movable and reversibly seals an opening of the storage container, and which has at least one centrally located metering opening for metering the substances in the storage container, the plunger including a separation device for particles wherein the storage container has a receptacle opposite the opening.

9. The metering device according to claim 8, wherein the storage containers have substantially identical lengths and different diameters.

10. The metering device according to claim 8, further comprising a device adapted to at least one of synchronously vibrate, shake, and rotate the plurality of metering elements.

* * * * *